United States Patent [19]

Sasaki et al.

[11] Patent Number: 4,933,376
[45] Date of Patent: * Jun. 12, 1990

[54] PHOTOPOLYMERIZABLE DENTAL COMPOSITION

[75] Inventors: Isao Sasaki; Nobuhiro Mukai, both of Hiroshima; Hitoshi Ige, Ohtake, all of Japan

[73] Assignee: Mitsubishi Rayon Company Limited, Tokyo, Japan

[ * ] Notice: The portion of the term of this patent subsequent to Aug. 9, 2005 has been disclaimed.

[21] Appl. No.: 184,803

[22] Filed: Apr. 22, 1988

[30] Foreign Application Priority Data

May 6, 1987 [JP] Japan .................. 62-110159
Jun. 19, 1987 [JP] Japan .................. 62-153021
Jun. 19, 1987 [JP] Japan .................. 62-153023

[51] Int. Cl.$^5$ ............................................. C08F 226/06
[52] U.S. Cl. ......................................... 522/14; 522/11; 526/261
[58] Field of Search ............ 522/14, 11; 526/261

[56] References Cited

U.S. PATENT DOCUMENTS

| | | | |
|---|---|---|---|
| 3,847,767 | 11/1974 | Kloczewski . | |
| 4,650,845 | 3/1987 | Hegel | 526/261 |
| 4,678,819 | 7/1987 | Sasaki et al. | 522/14 |
| 4,762,863 | 8/1988 | Sasaki et al. | 523/116 |

FOREIGN PATENT DOCUMENTS

| | | |
|---|---|---|
| 12535 | 6/1980 | European Pat. Off. . |
| 17151 | 10/1980 | European Pat. Off. . |
| 17937 | 10/1980 | European Pat. Off. . |
| 59649 | 9/1982 | European Pat. Off. . |

Primary Examiner—John C. Bleutge
Assistant Examiner—Susan Berman
Attorney, Agent, or Firm—Oblon, Spivak, McClelland, Maier & Neustadt

[57] ABSTRACT

A photopolymerizable dental composition, which comprises:

(A) an organic composite filler obtained by polymerizing a sulfonic acid or sulfonate monomer of the formula:

$$H_2C=\underset{R_1}{\overset{|}{C}}-X-SO_3Y \quad (I)$$

wherein $R_1$ is a hydrogen atom, a $C_1$-$C_{20}$ alkyl group, a phenyl group or a derivative thereof, or a halogen atom;

X is $-CONH-$, $-CONH-\underset{R_3}{\overset{R_2}{\underset{|}{\overset{|}{C}}}}-R_4-$, $-COO(CH_2)_{\overline{m}}$ or $-(CH_2)_{\overline{n}}$ wherein each of $R_2$ and $R_3$ is a hydrogen atom or a $C_1$-$C_{15}$ alkyl group, $R_4$ is a $C_1$-$C_{15}$ alkylene group, m is an integer of from 1 to 20 and n is an integer of from 0 to 20; and Y is a hydrogen atom, $NH_4$ or an alkali metal atom, and at least one radical polymerizable vinyl monomer in a polymerization system in which an inorganic compound is dispersed;

(B) a monomer mixture comprising 2,2-bis[4-(methacryloxyethoxy)phenyl]propane, at least one hexafunctional urethane (meth)acrylate of the formula:

(II)

[structure of 1,3,5-triazine-2,4,6-trione ring with three X substituents on the ring nitrogens]

wherein X is $-(CH_2)_{\overline{n}}HNCOO-CH\underset{CH_2OOC-\underset{R_2}{\overset{|}{C}}=CH_2}{\overset{CH_2OOC-\underset{R_1}{\overset{|}{C}}=CH_2}{\diagup}}$ wherein n is an integer of from 1 to 10, and each of $R_1$ and $R_2$ which may be the same or different is a hydrogen atom or a methyl group, and a diluting ethylenic vinyl monomer; and (C) a photopolymerization initiator comprising an α-diketone compound and a reducing agent, wherein the reducing agent is at least one member selected from the group consisting of diaminobenzophenone compounds of the formula:

(III)

[structure of 4,4'-bis(amino)benzophenone: $R_1R_2N$-phenyl-C(=O)-phenyl-$NR_3R_4$]

wherein each of $R_1$ to $R_4$ which may be the same or different is a hydrogen atom or a $C_1$-$C_5$ alkyl group, provided that at least one of them is the alkyl group, and $C_5$-$C_{10}$ alkyl esters of 4-(N,N-dimethylamino)benzoic acid.

5 Claims, No Drawings

PHOTOPOLYMERIZABLE DENTAL COMPOSITION

The present invention relates to a dental filling composition containing a substantial amount of an organic composite filler as inorganic material. More particularly, it relates to a photopolymerizable dental filling composition which can readily be polymerized by irradiation with a visible light to provide a cured product having high mechanical properties and excellent water resistance.

For dental filling material, it is important that such material has not only good physical properties such as mechanical strength, abrasion resistance, water resistance and adhesive properties but also aesthetical properties such as transparency and polishability to make it look like natural teeth. Many attempts have been made to develop a so-called composite resin having an inorganic filler incorporated into a resin, as a substitute material for amalgam and with an object to improve the above-mentioned properties.

This composite resin is usually composed essentially of three components of (1) an inorganic filler, (2) an olefinic unsaturated compound and (3) a polymerization initiator. However, if an inorganic filler and an organic resin are simply blended, it is difficult to obtain adequate composite properties since the inorganic filler and the organic resin are poor in the interfacial affinity such as the compatibility or the adhesion to each other. In order to overcome such a drawback, a dental material has been proposed in which a filler prepared by treating a glass surface with a silane coupling agent is incorporated. However, the surface treatment with a silane coupling agent is limited in its applicable inorganic material to a glass filler having silanol groups on its surface and thus has a serious drawback that it is poor in the general applicability. Further, there is a problem such that the formed siloxane linkage is susceptible to hydrolysis and thus is poor in the water resistance. Accordingly, when applied to a dental filling composition, it hardly provides an interfacial reinforcing property to a quartz filler which is commonly employed as a filler to impart primarily high hardness and aesthetical properties. Further, it has a clinical problem such that since the water resistance is poor, the mechanical strength tends to deteriorate as time passes during clinic for a long period of time in a wet oral cavity.

Further, various studies have been made on the monomer constituting the organic resin. For example, a bisphenol A multi-functional monomer represented by bisphenol A diglycidyl methacrylate (hereinafter referred to simply as Bis-GMA) has been proposed as a monomer which provides a composite having a small polymerization shrinkage factor, and a hydrophobic monomer 2,2-bis[4-(methacyloxyethoxy)-phenyl]propane (hereinafter referred to simply as Bis-MEPP) has been proposed as a monomer which provides excellent water resistance. However, Bis-GMA has a hydroxyl group in its molecule, and the resulting cured product is highly water absorptive and thus is poor in the water resistance. On the other hand, when Bis-MEPP is used, the curability is poor and adequate crosslinking density is hardly obtainable, and there has been a problem that the product is poor in the mechanical strength. Further, even if Bis-GMA and Bis-MEPP are combined to complement these drawbacks, it is impossible to obtain a composite resin having satisfactory properties. Accordingly, in order to determine a monomer composition for a particular purpose, it is necessary to study a very wide range of monomer compositions.

It is an object of the present invention to provide a photopolymerizable dental composition having excellent mechanical strength and good water resistance.

The present invention provides a photopolymerizable dental composition, which comprises:

(A) an organic composite filler obtained by polymerizing a sulfonic acid or sulfonate monomer of the fomula:

wherein $R_1$ is a hydrogen atom, a $C_1$-$C_{20}$ alkyl group, a phenyl group or a derivative thereof, or a halogen atom;

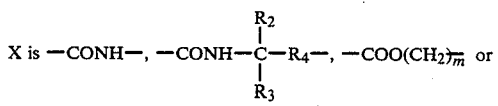

wherein each of $R_2$ and $R_3$ is a hydrogen atom or a $C_1$-$C_{15}$ alkyl group, $R_4$ is a $C_1$-$C_{15}$ alkylene group, m is an integer of from 1 to 20 and n is an integer of from 0 to 20; and Y is a hydrogen atom, $NH_4$ or an alkali metal atom, and at least one radical polymerizable vinyl monomer in a polymerization system in which an inorganic compound is dispersed;

(B) a monomer comprising 2,2-bis[4-(methacryloxyethoxy)phenyl]propane, at least one hexa-functional urethane (meth)acrylate of the formula:

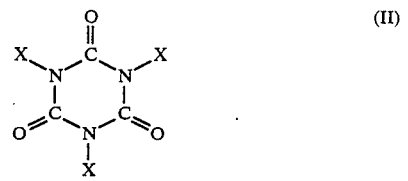

wherein X is

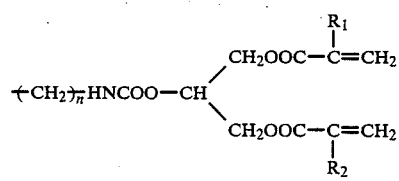

wherein n is an integer of from 1 to 10, and each of $R_1$ and $R_2$ which may be the same or different is a hydrogen atom or a methyl group, and a diluting ethylenic vinyl monomer; and (C) a photopolymerization initiator comprising an α-diketone compound and a reducing agent, wherein the reducing agent is at least one member selected from the group cosisting of diaminobenzophenone compounds of the formula:

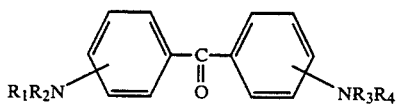

(III)

wherein each of $R_1$ to $R_4$ which may be the same or different is a hydrogen atom or a $C_1$–$C_5$ alkyl group, provided that at least one of them is the alkyl group, and $C_5$–$C_{10}$ alkyl esters of 4-(N,N-dimethylamino)benzoic acid.

Now, the present invention will be described in detail with reference to the preferred embodiments.

The organic composite filler (A) constituting the composition of the present invention can be obtained by polymerizing the sulfonic acid or sulfonate monomer with at least one other polymerizable vinyl monomer in a polymerization system in which an inorganic compound is dispersed. There is no particular restriction as to the method for its preparation. As a preferred embodiment, a method may be mentioned wherein a vinyl monomer and an inorganic compound are suspended and dispersed in an aqueous medium under such a temperature condition that no thermal polymerization takes place, and then, the sulfonic acid or sulfonate monomer is added and stirred to initiate aqueous heterogeneous polymerization, whereby the polymerization is conducted for a predetermined period of time.

In the above polymerization, a radical polymerization initiator may be added as the case requires. For example, it is preferred to add a radical polymerization initiator when a high graft rate is required or when a mixture of various vinyl monomers is used.

The specific sulfonic acid or sulfonate monomer represented by the formula I to be used for the formation of the organic composite filler (A) is required to have a sulfonic acid group as an active site which brings about the polymerization activity and a double bond as an active site which provides firm consolidation of the resulting polymer and the inorganic compound. Any compound of the polymer and the inorganic compound. Any compound of the formula I having such functional groups can be used. Specifically, 2-acrylamide-2-methylpropane sulfonic acid, sodium 2-methacrylethane sulfonate, sodium 3-methacrylpropane sulfonate, sodium 2-propane sulfonate and sodium 2-methyl-2-propane sulfonate may be mentioned. Among them, 2-acrylamide-2-methylpropane sulfonic acid containing an amide bond and sodium 2-methacrylethane sulfonate and sodium 3-methacrylpropane sulfonate containing an ester bond are particularly preferred since they are capable of providing remarkable secondary agglomeration and they have very high polymerization activities.

The inorganic compound to be used for the preparation of the organic composite filler (A) includes elements of Groups I, II, III, IV and V of the Periodic Table, transition metals and their oxides, hydroxides, chlorides, sulfates, sulfites, carbonates, phosphates and silicates, and mixtures and complex salts thereof. Among them, barium sulfate, barium fluoride, silicon dioxide, aluminum oxide, titanium oxide, quartz powder, glass powder, glass beads, glass fibers, a glass filler containing a barium salt, a lead salt or a strontium salt, silica gel, zirconium oxide and tin oxide are particularly preferred since they provide particularly excellent effects for activating the vinyl monomer and for firm consolidation with the polymer. It is one of the features of the present invention that the present invention is applicable to an inorganic compound to which usual coupling treatment is not applicable, and the shape and the size of the inorganic compound can suitably be selected.

As the vinyl monomer for the preparation of the organic composite filler (A) of the present invention, any usual radically polymerizable vinyl monomer may be used. Specifically, the vinyl monomer includes alkyl esters of (meth)acrylic acid such as methyl methacrylate and butyl acrylate; aromatic vinyl monomers such as styrene and α-methyl styrene; vinyl cyanide monomers such as acrylonitrile and methacrylonitrile; and monomers useful as the ethylenic vinyl monomer mixture (B) in the present invention. The monomer is suitably selected depending upon the particular purpose.

The radical polymerization initiator to be used for the preparation of the organic composite filler (A) may be any usual peroxide or azo compound. However, it is preferred to employ a radical polymerization initiator which is decomposable within a temperature range of from 40° to 100° C. Among them, peroxides such as benzoyl peroxide, and potassium persulfate and azo compounds such as azobisisobutylonitrile are particularly effective and preferred in view of the graft rate of the resulting organic composite filler.

The concentration of the sulfonic acid or sulfonate monomer for the preparation of the organic composite filler (A) is usually from about 0.05 to 100% by weight, preferably from 0.1 to 50% by weight, more preferably from 0.5 to 30% by weight, based on the total weight of the inorganic compound and the vinyl monomer. In many cases, it is preferred to increase the amount of the sulfonic acid or sulfonate monomer as the vinyl monomer component increases. The weight ratio of the vinyl monomer or a mixture of vinyl monomers to the inorganic compound used may be varied within a wide range and is usually within a rang of from about 500:1 to about 1:5, preferably from about 50:1 to about 1:1. When the polymerization is conducted in an aqueous medium, the amount of water is usually from about 1% to several hundreds times, preferably from about 10% to 10 times, based on the total weight of the inorganic compound and the vinyl monomer.

The reaction is preferably conducted in an atmosphere of an inert gas such as nitrogen usually at a temperature of from about 10° to 100° C., preferably at a temperature of about 40° to 100° C. at which the radical polymerization initiator can be decomposed. Here, the practical reaction temperature is suitably selected depending upon the vinyl monomer. However, it is important to conduct the reaction at a controlled temperature where thermal polymerization is negligible. If the reaction is conducted at a high temperature where thermal polymerization takes place substantially, the consolidation and the uniformity of the resulting composite filler will be impaired. The reaction time is usually from 30 minutes to about 15 hours. The resulting organic composite filler may be dried usually within a temperature range of from about 10° to 300° C., preferably from about 50° to 200° C. The interaction between the surface of the inorganic compound and the polymer provided by the method of the present invention is beyond a usual physical adhesion due to simple adsorption or van der Waals force. This is evident from the fact that a substantial amount of non-extracted polymer remains even when the vinyl polymer is subjected to extraction treatment with a good solvent.

In the above-mentioned organic composite filler (A), various inorganic compounds can be firmly consolidated with an organic polymer. Thus, the compatibility of the inorganic compound and the organic polymer in the composite resin is good, and the inorganic compound required for a dental composition can optionally be selected depending upon the particular purpose to obtain a dental composition as the desired product of the present invention.

The ethylenic vinyl monomer mixture (B) to be used in the present invention contains Bis-MEPP and a hexa-functional urethane (meth)acrylate of the formula II. By the combination of the two types of monomers, it is surprisingly possible to obtain a composite resin having excellent mechanical strength and good water resistance when the composition of the present invention is cured.

Among the monomers of the formula II, a hexa-functional urethane acrylate wherein n is 6, $R_1$ is a hydrogen atom and $R_2$ is a methyl group (hereinafter referred to simply as U-6HA) and a hexa-functional urethane methacrylate wherein n is 6 and each of $R_1$ and $R_2$ is a methyl group (hereinafter referred to simply as U-6H) are preferred from the viewpoint of curability. Among them, U-6HA is most preferred.

In the present invention, there is no particular restriction as to the proportions of Bis-MEPP, the hexa-functional urethane (meth)acrylate and the diluting ethylenic vinyl monomer in the monomer mixture (B). However, from the viewpoint of the operation efficiency for handling the composition of the present invention, it is preferred to adjust the proportions so that the viscosity of the composition of the present invention would be from 1,000 to 500,000 poise at 25° C. Usually, the proportions of Bis-MEPP and the hexa-functional urethane (meth)acrylate in the monomer mixture (B) are from 40 to 70% by weight and from 10 to 40% by weight, respectively. Further, from the viewpoint of the water resistance and mechanical strength, the blend ratio (weight ratio) of the hexa-functional urethane (meth)acrylate to Bis-MEPP is usually from 0.05:1 to 1:1, preferably from 0.1:1 to 0.8:1, more preferably from 0.2:1 to 0.5:1.

As the diluting ethylenic vinyl monomer for the present invention, the conventional monomers commonly employed for dental composite resins may be used. Specific examples include alkanediol (meth)acrylates such as triethylene glycol dimethacrylate and 1,6-hexamethylene glycol dimethacrylate; polyalkylene glycol di(meth)acrylates such as triethylene glycol dimethacrylate (hereinafter referred to simply as 3G) and tetraethylene glycol di(meth)acrylate; alkyl esters of (meth)acrylic acid such as trimethylolpropane tri(meth)acrylate, glycidyl (meth)acrylate, methyl methacrylate and butyl acrylate; aromatic hydrocarbons such as styrene and a-methyl styrene; and vinyl cyanide compounds such as acrylonitrile and methacrylonitrile. In the present invention, the radical polymerizable vinyl monomer used in the organic composite filler (A) and the monomer mixture (B) may be the same.

The proportions of the organic composite filler (A) and the monomer mixture (B) may optionally be selected depending upon the types and the purposes of the inorganic compound used for the filler (A) and the monomer mixture (B). However, the organic composite filler (A) and the monomer mixture (B) are used usually within the ranges of from 20 to 90 parts by weight and from 10 to 80 parts by weight, respectively.

There is no particular restriction as to the α-diketone compound to be used for the photopolymerization initiator (C) in the present invention. However, in view of its dental use in the oral cavity, it is preferably operable with a visible light having a wavelength of from 400 to 800 nm excluding the near ultraviolet region. Further, from the clinical standpoint, it is preferably curable in about 30 seconds.

From the foregoing points, preferred compounds include α-diketone compounds such as camphor quinone (hereinafter referred to simply as CQ), benzyl and diacetyl, and a mixture thereof. The α-diketone compound can be used in combination with a reducing agent. In the composition of the present invention, the reducing agent is required to be at least one member selected from the group consisting of diaminobenzophenone compounds of the formula:

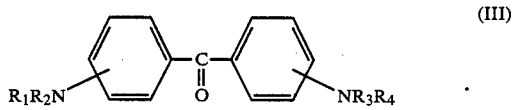

wherein each of $R_1$ to $R_4$ which may be the same or different is a hydrogen atom or a $C_1$–$C_5$ alkyl group, provided that at least one of them is the alkyl group, and $C_5$–$C_{10}$ alkyl esters of 4-(N,N-dimethylamino)benzoic acid. Among them, 4,4'-bis(dimethylamino)benzophenone (hereinafter referred to simply as AB) wherein each of $R_1$ to $R_4$ is a methyl group or isoamyl 4-(N,N-dimethyamino)benzoate (hereinafter referred to simply as DABA) is particularly preferred from the viewpoint of curability.

The amount of the photopolymerization initiator (C) is suitably selected taking into consideration the curability, the storage stability and the color tone of the compositon. However, the initiator is used usually in such an amount that the α-diketone compound is from 0.01 to 15% by weight, preferably from 0.05 to 5% by weight, more preferably from 0.1 to 2% by weight, relative to the monomer mixture (B), and the reducing agent is within a range of from 0.01 to 15% by weight, relative to the monomer mixture (B).

In addition to the above components, a filler may be added to the composition of the present invention, as the case requires. Such a filler component includes elements of Groups I, II, III, ,IV and V, transition metals and their oxides, hydroxides, chlorides, sulfates, sulfites, carbonates, phosphates and silicates, and mixtures and complex salts thereof. Among them, silicon dioxide, quartz powder, aluminum oxide, barium sulfate, titanium oxide, talc, glass powder, glass beads, glass fibers, a glass filler containing a barium salt or a lead salt, silica gel, colloidal silica, carbon fibers, zirconium oxide, tin oxide and other ceramics powders are preferred. The above filler may be a non-treated filler, a filler having its surface treated with e.g. a silane coupling agent or an organic composite filler obtained by consolidating a filler with a polymer, followed pulverization.

The amount of the filler to be incorporated can be suitably changed depending upon the particular purpose of the photopolymerizable dental composition. However, the filler is usually incorporated in an amount within a range of from 0.1 to $10^3$% by weight, preferably from 0.5 to $5 \times 10^2$% by weight, more preferably from 1 to $10^2$% by weight, relative to the above-mentioned monomer mixture (B) to form a paste composition.

Further, a coloring agent, a polymerization inhibitor (such as hydroquinone, methoxybenzophenone, methylphenol or hydroquinone monomethyl ether), an oxidation stabilizer, an ultraviolet absorber (such as benzophenone), a pigment (such as iron oxide or titanium oxide) and a dyestuff may further be incorporated to the composition of the present invention, as the case requires.

Now, the present invention will be described in further detail with reference to Examples. However, it should be understood that the present invention is by no means restricted to such specific Examples. In the Examples, "parts" means "parts by weight".

Preparation of organic composite fillers

Organic composite filler (1)

In a 500 ml four necked separable flask equipped with a condenser, a nitrogen supply tube, a stirrer and a thermo couple for detecting the internal temperature, 50 g of fine quartz powder (prepared by pulverizing quartz A-2 manufactured by Tatsumori K.K. to an average particle size of from 1 to 2 μm) and 50 g of barium glass (prepared by pulverizing barium glass #7724 manufactured by Corning Company to an average particle size of from 1 to 2 μm) were suspended and dispersed as the inorganic compounds in 290 ml of deionized water and flushed with nitrogen for 30 minutes. Then, 3.0 g of methyl methacrylate was added as the vinyl monomer while vigorously stirring under a nitrogen atomsphere to obtain a suspension. Then, the suspension was heated to 70° C. in a warm water bath. After confirming that the suspension was in a uniformly dispersed state, a solution obtained by dissolving 0.5 g of sodium 2-methacrylethane sulfonate as the sulfonate monomer in 10 ml of deionized water, was gradually added, and the polymerization reaction was conducted at the same temperature for 8 hours.

After the completion of the reaction, the product was collected by filtration under reduced pressure, thoroughly washed with water and then dried by hot air drying at 100° C. to remove the moisture to obtain about 100 g of an organic composite filler (1). The composite filler thus obtained had a polymer content of 2.6% as measured by a baking method, and when it was subjected to a Soxhlet extraction test for 50 hours by using hot benzene as the extracting solvent, the polymer content after the extraction was 2.2%. Thus, it was found that the majority of the polymer in the composite filler was extremely firmly consolidated to the surface of the fine quartz powder and barium glass. Separately, 100 g of each of the fine quartz powder and the barium glass was polymerized in the same manner independently, whereby the resulting product had the same polymer content as in the case of the combined system. Therefore, it is considered that the two inorganic fillers in the combined system have their surfaces uniformly consolidated with the polymer.

Organic composite filler (2)

An organic composite filler (2) was prepared in the same manner as in the preparation of the organic composite filler (1) except that 2-acrylamide-2-methylpropane sulfonic acid was used instead of sodium 2-methacrylethane sulfonate, and the evaluation was conducted in the same manner as in the case of the filler (1). The filler (2) thereby obtained showed the same results as the filler (1), thus indicating uniform consolidation.

Organic composite filler (3)

Into a 500 ml four necked separable flask equipped with a condenser, a nitrogen supply tube, a stirrer and a thermo couple for detecting the internal temperature, 50 g of fine quartz powder (prepared by pulverizing quartz A-2 manufactured by Tatsumori K. K. to an average particle size of from 1 to 2 μm) and 50 g of barium glass (prepared by pulverizing barium glass #7724 manufactured by Corning Company to an average particle size of from 1 to 2 μm) were suspended and dispersed as the inorganic compounds in 290 ml of deionized water and flushed with nitrogen for 30 minutes. Then, 2.5 g of methyl methacrylate was added as the vinyl monomer while vigorously stirring under a nitrogen atomsphere to obtain a suspension. Then, the suspension was heated to 70° C. in a warm water bath. After confirming that the suspension was in a uniformly dispersed state, a solution prepared by dissolving 0.5 g of sodium 2-methacrylethane sulfonate as the sulfonate monomer in 10 ml of deionized water and a solution prepared by dissolving 0.07 g of benzoyl peroxide as the radical polymerization initiator in 0.5 g of methyl methacrylate were gradually added, and the polymerization reaction was conducted at the same temperature for 8 hours.

After the completion of the reaction, the product was collected by filtration under reduced pressure, thoroughly washed with water and then dried by hot air drying at 100° C. to remove the moisture to obtain about 100 g of an organic composite filler (3). The composite filler thus obtained had a polymer content of 3.3% as measured by a baking method, and when it was subjected to a Soxhlet extraction test for 50 hours by using hot benzene as the extracting solvent, the polymer content after the extraction was as high as 3.1%. Thus, it was found that the majority of the polymer in the composite filler was extremely firmly consolidated to the surface of the fine quartz powder and barium glass. Separately, 100 g of each of the fine quartz powder and the barium glass was polymerized in the same manner independently, whereby the resulting product had the same polymer content as in the case of the combined system. Therefore, it is considered that the two inorganic fillers in the combined system have their surfaces uniformly consolidated with the polymer.

Organic composite fillers (4) to (6)

Organic composite fillers (4) to (6) were prepared in the same manner as the organic composite filler (3) except that 2-acrylamide-2-methylpropane sulfonic acid was used instead of sodium 2-methacrylethane sulfonate, butyl acrylate was used instead of methyl methacrylate, and azobisisobutyronitrile was used instead of benzoyl peroxide, respectively, and the evaluation was conducted in the same manner as in the case of the filler (3). The fillers (4) to (6) thus obtained showed the same results as the filler (3), thus indicating that they were uniformly consolidated.

To 90 g of each of the organic composite fillers (1) to (6) obtained by the methods as described above, 10 g of "Aerosil" (trade mark) R-972 (hydrophobic amorphous silica manufactured by Deutsche Gold-Und Silber-Scheideanstalt Vormals Roessler) filler to obtain fillers (A) to (F).

EXAMPLES 1 to 12 and COMPARATIVE EXAMPLES 1 to 4

Each of various photopolymerizable dental compositions prepared to have the composition as identified in Tables 1 and 2, was filled in a stainless steel mold having an inner diameter of 4 mm and a height of 6 mm, and a cover glass having a thickness of about 0.1 mm was fitted on each of the top and lower surfaces. Then, by using a visible light irradiator ("Optilux" manufactured by Minnesota Mining and Manufacturing Company, irradiation was conducted from both the top and lower surfaces for 30 seconds with a distance between the cover glass and the irradiator of 1 mm to obtain a cured product. The cured product thus obtained was stored in water at 37° C. for 24 hours, whereupon the compression strength was measured. Further, the cured product was stored in water at 37° C. for one week, whereupon the compression strength was evaluated as the water resistance strength. The strength was measured at a cross head speed of 1.0 mm/min. by using Tensilone (IS-500 manufactured by Shimadzu Corporation).

Further, a cured product obtained in the same manner by using a stainless steel mold having an inner diameter of 20 mm and a height of 1 mm was stored in water at 37° C. for one week. Then, the weight increase per unit surface area of the cured product was measured to evaluate the water absorption.

For the purpose of comparison, similar evaluation was conducted with respect to a case (a) wherein 10 g of "Aerosil" (trade mark) R-972 was mixed to 90 g of a silane-treated filler obtained by treating a filler mixture comprising 50 g of fine quartz powder and 50 g of barium glass with 3% of a silane coupling agent (3-methacryloxypropyltrimethoxysilane, KBM #503 manufactured by Shinetsu Silicon K.K.), instead of the composite filler of the present invention and a case of a non-treated filler (b) prepared by mixing 10 g of "Aerosil" (trade mark) R-972 to 45 g of each of non-treated fine quartz powder and barium glass.

It is evident from Tables 1 and 2 that dental materials using the composite fillers (A) to (F) of the present invention (Examples 1 to 12) provide cured products having superior mechanical strength and water resistance as compared with those wherein the conventional silane-treated fillers (Comparative Examples 1 and 3) or non-treated fillers (Comparative Examples 2 and 4) are used.

Further, the composite fillers used in the present invention had extremely good wettability with the monomer mixtures (B) and could readily be consolidated with the mixtures (B) to form uniform composites. Besides, the outer appearance of the cured products thereby obtained were substantially superior to the Comparative Examples. EXAMPLES 13 and 15 and COMPARATIVE EXAMPLES 5 to 8

Aqueous heterogeneous polymerization was conducted in the same manner as in Example 1 except that 100 g of aluminum oxide powder (special grade reagent) as the inorganic compound to obtain an organic composite filler (G). The composite filler thus obtained had a polymer content of 2.6%, and the polymer content after the extraction treatment was 2.2%. By using this organic composite filler (G), dental compositions were prepared to have the compositions as identified in Tables 3 and 4, and various physical properties of the cured products were evaluated in the same manner as in Example 1. The results thereby obtained are shown in Tables 3 and 4.

For the purpose of comparison, evaluation in the same manner as in Example 1 was conducted with respect to a case wherein a silane treated filler (c) obtained by treating aluminum oxide powder with 3% of a silane coupling agent was used instead of the composite filler of the present invention and a case wherein non-treated aluminum oxide powder (d) was used instead of the composite filler of the present invention.

EXAMPLES 14 and 16

Aqueous heterogeneous polymerization was conducted in the same manner as in Example 3 except that 100 g of aluminum oxide powder (special grade reagent) was used as the inorganic compound to obtain an organic composite filler (H). The composite filler thus obtained had a polymer content of 3.3%, and the polymer content after the extraction treatment was 3.0%. By using this organic composite filler (H), dental compositions were prepared to have the compositions as identified in Tables 3 and 4, and various physical properties of the cured products were evaluated in the same manner as in Example 3. The results thereby obtained are shown in Tables 3 and 4.

It is evident from Tables 3 and 4 that like the results in the Tables 1 and 2, those wherein the dental compositions of the present invention were used have superior properties as compared with those wherein the conventional silane-treated fillers or non-treated fillers were employed.

EXAMPLES 17 to 19 and 25 to 27 and COMPARATIVE EXAMPLES 9 to 11 and 17 to 19

Dental compositions were prepared in the same manner as in Examples 1 and 7 except that the composition of the monomer mixture (B) was changed as shown in Tables 5 and 6, and various physical properties of the cured products thereby obtained were evaluated in the same manner as in Example 1. The results are shown in Tables 5 and 6.

EXAMPLES 20 to 24 and 28 to 32 and COMPARATIVE EXAMPLES 12 to 16 and 20 to 24

Dental compositions were prepared in the same manner as in Examples 3 and 9 except that the composition of the monomer mixture (B) was changed as shown in Tables 5 and 6, and various physical properties of the cured products thereby obtained were evaluated in the same manner as in Example 3.

The results are shown in Tables 5 and 6.

It is evident from Tables 5 and 6 that by using specific monomers as the monomer mixture (B), it is possible to obtain cured products for dental use having excellent mechanical strength and water resistance.

EXAMPLES 33 and 34 and COMPARATIVE EXAMPLES 25 and 26

Dental compositions were prepared in the same manner as in Examples 1 or Comparative Example 1 except that the reducing agent was changed as shown in Table 7 and, various physical properties of the cured products thereby obtained were evaluated in the same manner as in Example 1.

The results are shown in Table 7.

EXAMPLES 35 and 36

Dental compositions were prepared in the same manner as in Example 3 except that the reducing agent was changed as shown in Table 7, and various physical properties of the cured products thereby obtained were evaluated in the same manner as in Example 3.

The results are shown in Table 7.

As described in detail in the foregoing, the composition of the present invention is excellent in the mechanical strength and water resistance and when used as a dental material composition, it exhibits excellent effects.

TABLE 1

| | Composition of photopolymerizable dental composition | | | | | | Physical properties of cured product | | |
|---|---|---|---|---|---|---|---|---|---|
| | Filler (A) | | Monomer mixture (B) (parts) | | | Photopolymerization initiator (C) (parts) (*1) | | Compressive strength (kg/cm²) | Water absorption (mg/cm²) | Water resistance strength (kg/cm²) |
| | Type | Amount (parts) | Bis-MEPP | U-6HA | 3G | CQ | AB | | | |
| Example 1 | A | 70 | 18 | 6 | 6 | 0.4 | 2.0 | 3320 | 0.18 | 3310 |
| Example 2 | B | " | " | " | " | " | " | 3310 | 0.19 | 3300 |
| Example 3 | C | " | " | " | " | " | " | 3400 | 0.17 | 3400 |
| Example 4 | D | " | " | " | " | " | " | 3370 | 0.20 | 3350 |
| Example 5 | E | " | " | " | " | " | " | 3340 | 0.17 | 3340 |
| Example 6 | F | " | " | " | " | " | " | 3390 | 0.18 | 3380 |
| Comparative Example 1 | a | 70 | 18 | 6 | 6 | 0.4 | 2.0 | 2920 | 0.44 | 2490 |
| Comparative Example 2 | b | " | " | " | " | " | " | 2180 | 0.33 | 1980 |

(*1) Amount relative to 100 parts of the monomer mixture (B).

TABLE 2

| | Composition of photopolymerizable dental composition | | | | | | | Physical properties of cured product | | |
|---|---|---|---|---|---|---|---|---|---|---|
| | Filler (A) | | Monomer mixture (B) (parts) | | | Photopolymerization initiator (C) (parts) (*1) | | Compressive strength (kg/cm²) | Water absorption (mg/cm²) | Water resistance strength (kg/cm²) |
| | Type | Amount (parts) | Bis-MEPP | U-6HA | 3G | CQ | DABA | | | |
| Example 7 | A | 70 | 18 | 6 | 6 | 0.4 | 2.0 | 3320 | 0.19 | 3320 |
| Example 8 | B | " | " | " | " | " | " | 3300 | 0.20 | 3280 |
| Example 9 | C | " | " | " | " | " | " | 3420 | 0.17 | 3420 |
| Example 10 | D | " | " | " | " | " | " | 3360 | 0.18 | 3350 |
| Example 11 | E | " | " | " | " | " | " | 3340 | 0.17 | 3340 |
| Example 12 | F | " | " | " | " | " | " | 3380 | 0.19 | 3370 |
| Comparative Example 3 | a | 70 | 18 | 6 | 6 | 0.4 | 2.0 | 2900 | 0.43 | 2500 |
| Comparative Example 4 | b | " | " | " | " | " | " | 2200 | 0.35 | 2000 |

(*1) Amount relative to 100 parts of the monomer mixture (B).

TABLE 3

| | Composition of photopolymerizable dental composition | | | | | | | Physical properties of cured product | | |
|---|---|---|---|---|---|---|---|---|---|---|
| | Filler (A) | | Monomer mixture (B) (parts) | | | Photopolymerization initiator (C) (parts) (*1) | | Compressive strength (kg/cm²) | Water absorption (mg/cm²) | Water resistance strength (kg/cm²) |
| | Type | Amount (parts) | Bis-MEPP | U-6HA | 3G | CQ | AB | | | |
| Example 13 | G | 30 | 42 | 14 | 14 | 0.4 | 2.0 | 1050 | 0.24 | 1030 |
| Example 14 | H | " | " | " | " | " | " | 1070 | 0.21 | 1070 |
| Comparative Example 5 | c | " | " | " | " | " | " | 380 | 0.58 | 280 |
| Comparative Example 6 | d | " | " | " | " | " | " | 420 | 0.45 | 300 |

(*1) Amount relative to 100 parts of the monomer mixture (B).

TABLE 4

| | Composition of photopolymerizable dental composition | | | | | | | Physical properties of cured product | | |
|---|---|---|---|---|---|---|---|---|---|---|
| | Filler (A) | | Monomer mixture (B) (parts) | | | Photopolymerization initiator (C) (parts) (*1) | | Compressive strength (kg/cm²) | Water absorption (mg/cm²) | Water resistance strength (kg/cm²) |
| | Type | Amount (parts) | Bis-MEPP | U-6HA | 3G | CQ | DABA | | | |
| Example 15 | G | 30 | 42 | 14 | 14 | 0.4 | 2.0 | 1040 | 0.23 | 1020 |
| Example 16 | H | " | " | " | " | " | " | 1080 | 0.20 | 1070 |
| Comparative | c | " | " | " | " | " | " | 390 | 0.59 | 290 |

TABLE 4-continued

| | Composition of photopolymerizable dental composition | | | | | | | Physical properties of cured product | | |
|---|---|---|---|---|---|---|---|---|---|---|
| | Filler (A) | | Monomer mixture (B) (parts) | | | Photopolymerization initiator (C) (parts) (*1) | | Compressive strength (kg/cm²) | Water absorption (mg/cm²) | Water resistance strength (kg/cm²) |
| | Type | Amount (parts) | Bis-MEPP | U-6HA | 3G | CQ | DABA | | | |
| Example 7 Comparative Example 8 | d | " | " | " | " | " | " | 410 | 0.45 | 300 |

(*1) Amount relative to 100 parts of the monomer mixture (B).

TABLE 5

| | Composition of photopolymerizable dental composition | | | | | | | | Physical properties of cured product | | |
|---|---|---|---|---|---|---|---|---|---|---|---|
| | Filler (A) | | Monomer mixutre (B) (parts) | | | | | Photopolymerization initiator (C) (parts) (*1) | Compressive strength (kg/cm²) | Water absorption (mg/cm²) | Water resistance strength (kg/cm²) |
| | Type | Amount (parts) | Bis-MEPP | Bis-GMA | U-6HA | U-6H | 3G | CQ / AB | | | |
| Example 17 | A | 70 | 18 | — | — | 6 | 6 | 0.4 / 2.0 | 3310 | 0.19 | 3300 |
| Example 18 | " | " | 11 | — | 13 | — | " | " / " | 3220 | 0.31 | 3220 |
| Example 19 | " | " | 22 | — | 2 | — | " | " / " | 3000 | 0.19 | 3000 |
| Example 20 | C | " | 18 | — | — | 6 | " | " / " | 3380 | 0.18 | 3380 |
| Example 21 | " | " | 11 | — | 13 | — | " | " / " | 3320 | 0.29 | 3310 |
| Example 22 | " | " | 22 | — | 2 | — | " | " / " | 3110 | 0.17 | 3100 |
| Example 23 | C | 70 | 20 | — | 4 | — | 6 | 0.4 / 2.0 | 3350 | 0.18 | 3340 |
| Example 24 | " | " | 16 | — | — | 8 | " | " / " | 3380 | 0.18 | 3370 |
| Comparative Example 9 | A | " | 24 | — | — | — | " | " / " | 2700 | 0.19 | 2670 |
| Comparative Example 10 | " | " | — | 24 | — | — | " | " / " | 3210 | 0.53 | 2840 |
| Comparative Example 11 | " | " | 12 | 12 | — | — | " | " / " | 2830 | 0.43 | 2490 |
| Comparative Example 12 | C | 70 | 24 | — | — | — | 6 | 0.4 / 2.0 | 2810 | 0.17 | 2800 |
| Comparative Example 13 | " | " | — | 24 | — | — | " | " / " | 3320 | 0.48 | 3000 |
| Comparative Example 14 | " | " | 12 | 12 | — | — | " | " / " | 2940 | 0.42 | 2800 |
| Comparative Example 15 | " | " | — | 18 | 6 | — | " | " / " | 3370 | 0.47 | 3050 |
| Comparative Example 16 | " | " | — | 18 | — | 6 | " | " / " | 3330 | 0.45 | 3040 |

(*1) Amount relative to 100 parts of the monomer mixture (B).

TABLE 6

| | Composition of photopolymerizable dental composition | | | | | | | | Physical properties of cured product | | |
|---|---|---|---|---|---|---|---|---|---|---|---|
| | Filler (A) | | Monomer mixture (B) (parts) | | | | | Photopolymerization initiator (C) (parts) (*1) | Compressive strength (kg/cm²) | Water absorption (mg/cm²) | Water resistance strength (kg/cm²) |
| | Type | Amount (parts) | Bis-MEPP | Bis-GMA | U-6HA | U-6H | 3G | CQ / DABA | | | |
| Example 25 | A | 70 | 18 | — | — | 6 | 6 | 0.4 / 2.0 | 3300 | 0.19 | 3300 |
| Example 26 | " | " | 11 | — | 13 | — | " | " / " | 3220 | 0.32 | 3220 |
| Example 27 | " | " | 22 | — | 2 | — | " | " / " | 3000 | 0.18 | 3000 |
| Example 28 | C | " | 18 | — | — | 6 | " | " / " | 3400 | 0.18 | 3380 |
| Example 29 | " | " | 11 | — | 13 | — | " | " / " | 3310 | 0.30 | 3300 |
| Example 30 | " | " | 22 | — | 2 | — | " | " / " | 3100 | 0.16 | 3100 |
| Example 31 | C | 70 | 20 | — | 4 | — | 6 | 0.4 / 2.0 | 3360 | 0.17 | 3350 |
| Example 32 | " | " | 16 | — | — | 8 | " | " / " | 3380 | 0.19 | 3360 |
| Comparative Example 17 | A | " | 24 | — | — | — | " | " / " | 2710 | 0.18 | 2670 |
| Comparative Example 18 | " | " | — | 24 | — | — | " | " / " | 3200 | 0.52 | 2850 |
| Comparative Example 19 | " | " | 12 | 12 | — | — | " | " / " | 2830 | 0.44 | 2500 |
| Comparative Example 20 | C | 70 | 24 | — | — | — | 6 | 0.4 / 2.0 | 2820 | 0.16 | 2800 |
| Comparative Example 21 | " | " | — | 24 | — | — | " | " / " | 3320 | 0.50 | 3020 |
| Comparative Example 22 | " | " | 12 | 12 | — | — | " | " / " | 2950 | 0.42 | 2800 |
| Comparative Example 23 | " | " | — | 18 | 6 | — | " | " / " | 3360 | 0.45 | 3060 |
| Comparative | " | " | — | 18 | — | 6 | " | " / " | 3340 | 0.46 | 3040 |

TABLE 6-continued

| | Composition of photopolymerizable dental composition | | | | | | | Physical properties of cured product | | |
|---|---|---|---|---|---|---|---|---|---|---|
| | Filler (A) | Monomer mixture (B) (parts) | | | | Photopolymerization initiator (C) (parts) (*1) | | Compressive strength (kg/cm²) | Water absorption (mg/cm²) | Water resistance strength (kg/cm²) |
| | Type | Amount (parts) | Bis-MEPP | Bis-GMA | U-6HA | U-6H 3G | CQ | DABA | | | |
| Example 24 | | | | | | | | | | | |

(*1) Amount relative to 100 parts of the monomer mixture (B).

TABLE 7

| | Composition of photopolymerizable dental composition | | | | | | | Physical properties of cured product | | |
|---|---|---|---|---|---|---|---|---|---|---|
| | Filler (A) | | Monomer mixture (B) (parts) | | | Photopolymeriaztion initiator (C) (parts) (*1) | | Compressive strength (kg/cm²) | Water absorption (mg/cm²) | Water resistance strength (kg/cm²) |
| | Type | Amount (parts) | Bis-MEPP | U-6HA | 3G | CQ | Reducing agent | | | | |
| | | | | | | | Type | Amount | | | |
| Example 33 | A | 70 | 18 | 6 | 6 | 0.4 | X (*2) | 2.0 | 3050 | 0.25 | 3010 |
| Example 34 | A | " | " | " | " | " | Y (*3) | " | 3150 | 0.24 | 3100 |
| Example 35 | C | " | " | " | " | " | X | " | 3100 | 0.24 | 3070 |
| Example 36 | C | " | " | " | " | " | Y | " | 3200 | 0.23 | 3140 |
| Comparative Example 25 | a | " | " | " | " | " | X | " | 2800 | 0.46 | 2420 |
| Comparative Example 26 | " | " | " | " | " | " | Y | " | 2900 | 0.42 | 2480 |

(*1) Amount relative to 100 parts of the monomer mixture (B).
(*2) X: Ethyl 4-(N,N-dimethylamino)benzoate
(*3) Y: Dimethylaminoethyl methacrylate

We claim:

1. A photopolymerizable dental composition, which comprises:

(A) an organic composite filler obtained by polymerizing a sulfonic acid or sulfonate monomer of the fomula:

$$H_2C=\underset{R_1}{\overset{|}{C}}-X-SO_3Y \quad (I)$$

wherein $R_1$ is a hydrogen atom, a $C_1$-$C_{20}$ alkyl group, a phenyl group or a derivative thereof, or a halogen atom;

X is $-CONH-$, $-CONH-\underset{R_3}{\overset{R_2}{\overset{|}{\underset{|}{C}}}}-R_4-$, $-COO(CH_2)_{\overline{m}}$ or

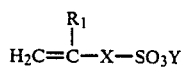

wherein each of $R_2$ and $R_3$ is a hydrogen atom or a $C_1$-$C_{15}$ alkyl group, $R_4$ is a $C_1$-$C_{15}$ alkylene group, m is an integer of from 1 to 20 and n is an integer of from 0 to 20; and Y is a hydrogen atom, $NH_4$ or an alkali metal atom, and at least one radical polymerizable vinyl monomer in a polymerization system in which an inorganic compound is dispersed;

(B) a monomer mixture comprising 2,2-bis[4-(methacryloxyethoxy)phenyl]propane, at least one hexafunctional urethane (meth)acrylate of the formula:

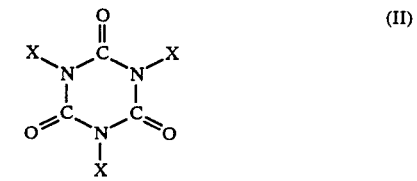

wherein X is $$+CH_2\xleftarrow{}_n HNCOO-CH\underset{CH_2OOC-\underset{R_2}{\overset{|}{C}}=CH_2}{\overset{CH_2OOC-\underset{R_1}{\overset{|}{C}}=CH_2}{\diagup}}$$

wherein n is an integer of from 1 to 10, and each of $R_1$ and $R_2$ which may be the same or different is a hydrogen atom or a methyl group, and a diluting ethylenic vinyl monomer; and (C) a photopolymerization initiator comprising an α-diketone compound and a reducing agent, wherein the reducing agent is at least one member selected from the group cosisting of diaminobenzophenone compounds of the formula:

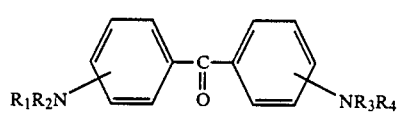

wherein each of $R_1$ to $R_4$ which may be the same or different is a hydrogen atom or a $C_1$-$C_5$ alkyl group, provided that at least one of them is the alkyl group, and $C_5$-$C_{10}$ alkyl esters of 4-(N,N-dimethylamino)benzoic acid.

2. The photopolymerizable dental composition according to claim 1, wherein the sulfonic acid or sulfonate monomer is 2-acrylamide-2-methylpropane sulfonic acid, sodium 2-methacrylethane sulfonate or sodium 3-methacrylpropane sulfonate.

3. The photopolymerizable dental composition according to claim 1, wherein the inorganic compound is at least one member selected from the group consisting of barium sulfate, barium fluoride, silicon dioxide, aluminum oxide, titanium oxide, quartz powder, glass powder, glass beads, glass fibers, a glass filler containing a barium salt, a lead salt or a strontium salt, silica gel, zirconium oxide and tin oxide.

4. The photopolymerizable dental composition according to claim 1, wherein the o-diketone compound is at least one member selected from the group consisting of camphor quinone, benzyl and diacetyl.

5. The photopolymerizable dental composition according to claim 1, wherein (A) comprises sodium 2-methacrylethane sulfonate and amorphous silica, (B) comprises 2,2-bis[4-methacryloxyethoxy)-phenyl]propane, a urethane acrylate wherein n is 6, $R_1$ is hydrogen and $R_2$ is methyl, and triethylene glycol dimethacrylate, and (C) comprises camphorquinone and isoamyl 4-(N,N-dimethylamino)benzoate.

* * * * *